United States Patent
Cobb

(10) Patent No.: US 6,329,149 B1
(45) Date of Patent: Dec. 11, 2001

(54) REVERSE-ROOT-CANAL METHOD FOR EXTRACTING ADNA

(76) Inventor: Janice Cori Cobb, 60 Pines LK. Dr. E., Wayne, NJ (US) 07476

(*) Notice: Subject to any disclaimer, the term of this patent is extended or adjusted under 35 U.S.C. 154(b) by 0 days.

(21) Appl. No.: 09/520,042

(22) Filed: Mar. 7, 2000

(51) Int. Cl.⁷ ............................... C12Q 1/68; A61C 5/02; A61C 3/02
(52) U.S. Cl. ............................ 435/6; 433/102; 433/224; 433/165
(58) Field of Search .............................. 435/6; 433/102, 433/224, 165

(56) References Cited

U.S. PATENT DOCUMENTS

| | | | |
|---|---|---|---|
| 5,676,541 | * 10/1997 | Maillefer et al. | 433/102 |
| 5,692,902 | * 12/1997 | Aeby | 433/102 |
| 6,096,498 | * 8/2000 | Agnello | 435/5 |
| 6,136,537 | * 10/2000 | Macevicz | 435/6 |
| 6,165,723 | * 12/2000 | Shah et al. | 435/6 |
| 6,168,918 | * 1/2001 | Satishchandran et al. | 435/6 |

OTHER PUBLICATIONS

Merriwether et al. "Genetic variation in the New World: ancient teeth, bone, and tissue as sources of DNA" Birkhauser Verlag Basel Experientia, vol. 50, No. 6, p. 592–601, Jun. 1994.*

Woodward et al. "Amplification of Ancient Nuclear DNA from teeth and soft tissues" PCR Methods and Applications, vol. 3, p. 244–247, 1994.*

Mornstad et al. "Demonstration and semi–quantification of mtDNA from human dentine and its relation to age" Int. J. Legal Med. vol. 112, p. 98–100, 1999.*

Zierdt et al. " Amplification of human STR from medieval teeth and bone samples" Human Biology, vol. 68, No. 2, p. 185–199, Apr. 1996.*

* cited by examiner

*Primary Examiner*—Lisa B. Arthur
*Assistant Examiner*—Jeanine Goldberg

(57) ABSTRACT

Teeth, the hardest substance in the human body, are frequently all that remain of a mortuary population from which direct human presence can be gleaned. As such their morphology is invaluable to physical anthropologists and investigators in allied disciplines. Methods currently used for purposes of extracting DNA from dental remains—e.g. bone-milling, crushing, and sectioning—result in total destruction of the teeth. This paper introduces the Reverse-Root-Canal, a protocol by which DNA of molecular weight higher than that obtainable through traditional destructive means, can be obtained from ancient dental remains without harm to the morphologically informative crown and roots.

1 Claim, 1 Drawing Sheet

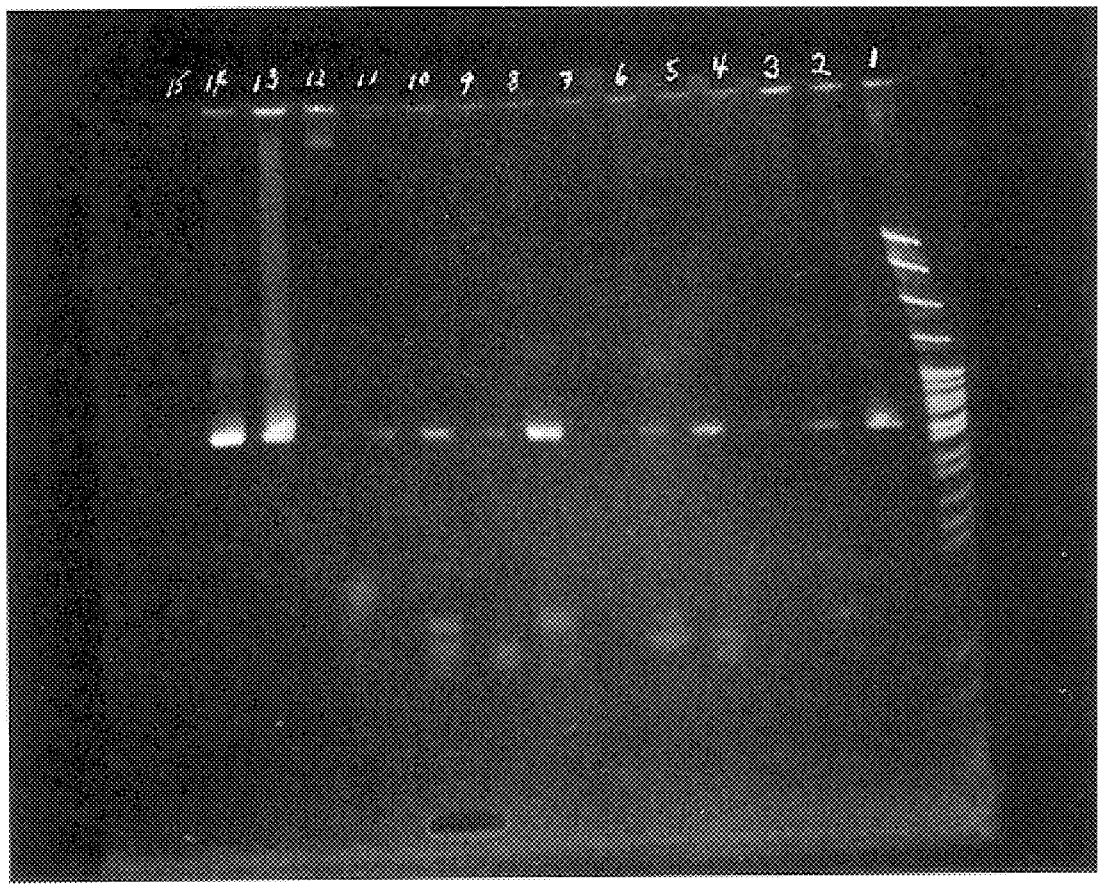

REVERSE-ROOT-CANAL METHOD FOR EXTRACTING ADNA

BACKGROUND OF THE INVENTION

Teeth, as the most durable tissue in the human body, are often all that remain of direct evidence for human occupation of an archaeological site. Dental remains are therefore prized by investigators from numerous disciplines, including physical anthropologists. Dental anthropologists assess teeth for morphological variants that characterize extinct as well as those by which extant populations can be identified (Scott and Turner, 1997).

Through such studies, connections between early hominids and extant primates with current human populations have also been made (Irish, 1998). Through analyses of dental use wear patterns, paleoecologists are able to reconstruct ancient environments. In so doing, new perspectives regarding human physiological as well as cultural adaptations in space and time can be gleaned (Walker, 1976; Grine and Kay, 1988). Depositional differences among skeletal and dental remains enable taphonomists to recreate early hominid paleo-environments (Behrensmeyer, 1975).

Through the assessment of dental stigmata, paleopathologists are able to identify diseases like congenital syphilis, and the existence of nutritional stressors among and between members of mortuary populations (Jacobi, et al., 1992; Katzenberg, 1993; Hillson, 1996; Scott and Turner, 1997; Langsjoen, 1998). Culturally motivated dental alterations (ogsley and Bellande, 1982; Scott and Turner, 1997; Langsjoen, 1998) in addition to environmentally associated occlusal and interproximal wear (Brace, 1975; Blakely and Beck, 1984; Bullington, 1991; Ungar and Spencer, 1999), are also discernable through assessment of dental remains.

This current study was undertaken ancillary to a multidisciplinary project under the auspices of the Chinese Institute of Archaeology, Chinese Academy of Social Sciences, and the Archaeometry Laboratory at the University of Minnesota, Duluth. The protocol described herein was devised to provide a means by which molecular investigations—e.g. mtDNA haplotypes from the Shang Dynasty Heiheru Site at Anyang, China—could proceed without compromising the integrity of morphologically informative dentition.

Molecular Investigations of Genetic Composition in China

To the extent that advances in the burgeoning field of molecular archaeology have engendered study of DNA from human remains, ancient DNA provides an added dimension to these investigations (Hagelberg, 1994). To this end, mitochondrial DNA (mtDNA) investigations (Cavalli-Sforza et al., 1967, 1988, 1994, 1998) have bolstered the impact of small migration events, such as may occur during trade on otherwise stable gene pools. Mitochondrial DNA analyses of Bronze-Age remains in northwestern China, Xinjiang (Zhao, 1998) and studies involving blood group antigens (Francalacci, 1998) support this hypothesis.

Even under the most adverse conditions, tissue derived from skeletal and dental remains generally contain fewer polymerase chain reaction (PCR) inhibitors than do soft tissue remains from the same specimen (Lassen et al., 1994). Comparative assays of both skeletal and soft tissue taken from Pre-Columbian South America mummies by Lassen et al., (1994), suggest that ancient DNA should preferentially be extracted from hard rather than soft tissues.

In dental remains, hydroxyapatite, the inorganic component of osseous tissue to which DNA preferentially binds, is present in higher concentrations than in skeletal remains. Furthermore, as teeth are considerably less susceptible to co-extracted contamination than skeletal remains (Zierdt, Hummel, Herrman, 1996), use of dental remains for ancient DNA analyses obviates one of ancient DNA study's most problematic concerns (Hagelberg, 1994).

BRIEF SUMMARY OF THE INVENTION

Since as little as 0.01 of a gram of dentin is required to yield aDNA of sufficient molecular height for study (DeGusta, Cook, Sensaubaugh, 1994), the Reverse-Root-Canal technique presented herein offers a non-destructive alternative to the methods currently practiced. Moreover, in addition to its ability to conserve much of the roots and the entire crown, the acquisition of aDNA by this method greatly curtails the amount of co-extracted contaminants (Smith et al., 1993).

BRIEF DESCRIPTION OF THE DRAWINGS

FIG. 1 illustrates a comparison of aDNA from dentin extracted via Reverse-Root-Canal as compared to teeth subjected to traditional bone-milling.

LEGEND FOR FIG. 1

Lane 1—Size Standard
Lane 2—Modern Control #1
Lane 3—#479Dentin only
Lane 4—#479Bone-Milled
Lane 5—#M30—Dentin Only
Lane 6—#M30—Bone-Milled
Lane 7—PCR Control
Lane 8—#655Dentin Only
Lane 9—#655Bone-Milled
Lane 10—#667a —Dentin Only
Lane 11—#667a —Bone-Milled
Lane 12—PCR Control
Lane 13—Modern Control #1
Lane 14—Modern Control #2
Lane 15—Extraction Control

METHODS AND MATERIALS

Population of Study

The dental remains analyzed and discussed in this paper were collected from the Heiheru Site lineage cemeteries from the last capital of the Shang Dynasty, Anyang, China. Dating of this Shang mortuary population (1300 BC to 1045 BC) was based on radiocarbon dating corroborated with pottery seriation (Chang, 1976), and with ancient Chinese writings (Tang, J., personal communication, 1999). Of the 30 teeth collected by J. E. Molto during the 1998 and 1999 field seasons, 29 were processed and analyzed in accordance with the protocol described herein. Although the 30th sample was extensively worn, compounding its poor state of preservation, in the main, these teeth were found to be in an excellent state of preservation. Inasmuch as the best predictor of the recovery of DNA from ancient remains is the preservation of the histological structure of the sample (Colson et al., 1996), the high degree of morphological integrity of these remains supports the probability that ancient DNA was indeed recovered. While most were devoid of carious lesions, many teeth evidenced considerable occlusal and interproximal attrition; however none of the pulp cavities were perforated.

Preparation of Individual Teeth for DNA Extraction

Due to its inherent sensitivity, the polymerase chain reaction (PCR) will preferentially amplify more robust biomolecules derived from modern human DNA rather than those from the ancient DNA template of interest (Hagelberg and Clegg, 1991; Poinar, et al., 1996; Evison, Smillie, Chamberlain, 1997). To avoid this problem, insofar as possible, elaborate measures (see Paabo, et al., 1990) were taken to avoid the incursion of contemporary human residues into DNA extractions. Furthermore, as an added precaution against exogenous contaminiation, prior to these analyses, I investigated the restriction enzyme site pattern by which my own mtDNA is characterized (Handt, et al., 1996). In addition to the preparatory treatment of each tooth described below, extractions and set-ups for PCR reactions were performed in a "clean room" located in a facility separate from that in which amplifications and post-PCR analyses were performed (Molto, 1999, in press).

Following removal from the individual sterile bag in which it was stored, each tooth was placed under a protective hood flooded with ultraviolet light where the following preliminary procedures were performed:

1. To remove superficial contamination from modern human DNA, each tooth was gently brushed with a solution of undiluted bleach applied with a soft-bristled tooth brush.
2. To prevent the bleach from eradicating endogenous ancient residues (Schwartz et al., 1991), each tooth was placed in a five ml receptacle containing autoclaved double-distilled water for five minutes. Prior to further preparation, the tooth was permitted to air dry for five minutes.

Although skeletal remains have traditionally been subjected to rigorous sandblasting to remove remnants of external contaminants prior to molecular assays (Hoss and Paabo, 1993), the fragility of dental remains requires special care (Schwartz, et al., 1991). To this end, a phosphoric acid gel, commonly used in clinical dental, practice, was applied to the external surface of the roots in such a manner as to avoid contact with the apices: thereby decreasing the possibility of its incursion into the root canals. Studies (Tylka, et al., 1994; Ariyaratnam, et al., 1997) have demonstrated that surfaces of teeth subjected to sandblasting are virtually indistinguishable from those treated with the phosphoric acid gel when viewed under a scanning electron microscope (S.E.M.). This product was therefore considered efficacious for the purpose of non-invasively eliminating surface contamination in lieu of potentially damaging sandblasting. The excess gel was gently removed with a Kimwipe, and soaked for two minutes in a five ml receptacle containing autoclaved double-distilled water. During the five minutes allocated to air drying, the size of the apices, for the purposes of selecting the appropriate endodontic files, was assessed.

Selection of Endodontic Files

Endodontic files, like those used in clinical practice during root-canal procedures, were selected in accordance with the general morphology and state of preservation of each tooth. To prevent contamination among specimens, a set of files was dedicated to each tooth. Prior to accessing the apices, lighting under the extraction hood was changed from ultraviolet to fluorescent to avoid destruction of fragile ancient biomolecules.

Reverse-Root-Canal, in contrast to clinical root-canal therapy, begins with the smallest endodontic files—e.g. #00—to enter the apices. As the procedure progresses, slightly larger files (the exact size of which is dependant on individual root morphology) were used to gently broaden the canals. Tapered, flexible titanium-nickle files were then used to gradually advance into the pulp chamber, directly beneath the enameled crown, where the dentin affords maximum protection from external contaminants.

As in clinical practice, the files were gently rotated in a clockwise fashion to cause minimal impact on root morphology, while gently opening, entering, and widening the canals. During this procedure and subsequent abrading of the root canals and pulp chamber, a receptacle was placed directly under the working area to maximize acquisition of loosened dentin.

The DNA Extraction

The harvested dentin gas then transferred from the receptacle into a tube containing an extraction medium composed of 0.5 EDTA and 1 M Tris (each autoclaved at a PH of 8), and Tween 20 (100% polyxysorbitan monolaureate of molecular biology grade). In accordance with protocol established by Paabo et al., (1990), an extraction control, containing only extraction medium, was prepared to confirm the absence of contamination.

Each tube containing dentin harvested from a single specimen gas then inoculated with 75 ul of Proteinase K (Promega). Proteinase K breaks down the constituent amino acids to render the DNA more amenable to binding to the silica spin columns during subsequent purification. The dentin was then incubated overnight at 55° Celsius.

Purification of the DNA gas accomplished through use of a commercially available kit, Wizard, through which a 69% recovery of dsDNA of 200 bp can typically be expected. With a bulb transfer pipette, 300 ul of dentin from each incubated sample was added to a 100 ul solution of Wizard Direct Purification Buffer, which was then added to one ml of resin. Using a Leur-lock syringe, the resultant slurry, comprised of the sample, Direct Purification Buffer, and resin, was then pushed through a Wizard silica mini-column. This procedure was done slowly to maximize binding of the DNA to the Wizard silica mini-column. The slurry was then centrifuged for two minutes at 10,000 g. DNA trapped within the Wizard silica mini-column was eluted with 100 ul of autoclaved double-distilled water. Following the addition of four ul of DNA buffer, the sample extract was complete. Co-extracted microbacterial DNA, common among severely degraded specimens (Evison, Smillie, Chamberlain, 1997; Rollo and Morota, 1999), can inhibit PCR amplification. To the extent that this problem can be prevented through use of a decreased template concentration, a ⅕ dilution of the sample was also made at this time; one ul of DNA buffer and 19 ul of autoclaved double-distilled water was added to five ul extracted from the purified sample extract.

PCR Amplification

The purified extracts, taken from each sample, were then amplified using each of the following primers: Alu I 5176, DdeI 10394/Alu I 10397, Hae III 663, Hinc II 13259 and the 9 base-pair deletion (located between the gene that codes for Cytochrome Oxidase and lysine transfer RNA in the mitochondrion). An aliquot of Master Mix (composed of DNA buffer, BSA, Magnesium sulfate and dNTPs), to which 5 ul of purified sample was added, was placed under a hood flooded with ultraviolet light.

Each mixture was then inoculated with five ul of chosen primer and 7.5 ul of Deep Vent polymerase. So as not to denature the delicate polymerase, upon its introduction to the mixture, the ultraviolet lighting was replaced with fluorescent. Following the addition of 20 ul of Master Mix to each well in the microtitre plate destined to receive a sample, five ul of each sample was loaded into the designated wells. To account for the inherent proclivity of PCR to amplify the more robust biomolecules derived from modern DNA, a PCR Control containing only Master Mix, the primers appropriate to each assay, and the Deep Vent polymerase gas prepared.

As previously mentioned, the Clean Room was dedicated to the highly sensitive pre-PCR functions. However, the post-PCR facility (where modern samples are stored and added to pre-assigned wells), is replete with exogenous nucleic acid residues. Thus, as a preventative measure, a drop of mineral oil is added to each sell prior to entering the facility.

To prevent the highly reactive polymerase from initiating the reaction outside the thermocycler, thereby allowing the primers to anneal to themselves causing primer-dimers, the microtitre plate was carried on ice to the post-PCR facility. At this time, modern control samples were added to the designated thermal sells prior to placing the microtitre plate into the thermocycler.

Yield Gel and Restriction Enzyme Digests

Following PCR amplification, each of the amplified samples was electrophoresed through a polyacrilamide gel that was treated with ethidium bromide, a stain that binds to DNA. Those samples that fluoresce when viewed on a transluminator under ultraviolet light were considered to have amplified. They were subsequently introduced to restriction enzymes complementary to the primers with which they had been amplified. The digestion procedure gas accomplished through use of Nanosep filters and NEB buffers and enzymes in accordance with standard protocol.

Results and Discussion

Comparison of the new protocol to traditional DNA Extraction Bone-Milling

Of the 30 teeth, 29 were processed in accordance with the protocol described in this paper. Of those 30, 23 yielded aDNA of molecular weight sufficient for subsequent analyses.

To substantiate the acquisition of ancient DNA by means of the Reverse-Root-Canal procedure, the roots of seven teeth that had consistently amplified were subjected to traditional bone-mill preparation for DNA extraction. Due to the abundance of DNA available from dentin through Reverse-Root-Canal, a substantial amount of dentin remained in the tooth for subsequent study via traditional bone-mill preparation. The sample cleaning protocol for this second procedure was identical to that of the first. The resultant ponder from each tooth was placed in Extraction Buffer in accordance with the protocol described above.

Sutcliffe's (1978) studies of the *Escheria coli* plasmid, pBR322 (the size standard used in this study), suggest that the brightness of bands generated electrophoretically from each of the samples is a direct indication of the amount of DNA present. Thus, a comparison of the brightness of bands generated from dentin extracted via Reverse-Root-Canal indicates they contain twice as much ancient DNA as those generated from teeth subjected to traditional bone-milling (FIG. 1).

In addition to its ability to acquire dentin in a non-destructive manner, the consistently stronger ancient DNA amplification possible with the Reverse-Root-Canal protocol further supports its merit in circumventing the deleterious effects of co-extracted microbacterial contaminants prevalent in degraded specimens (Ginter, et al., 1992; Evison, Smille and Chamberlain, 1997). Furthermore, in addition to the precautions discussed earlier, because there were no DNA bands present in either the extraction control of the PCR controls (FIG. 1), it can be assumed that no contamination was present (Yang, et al, 1998).

Discussion of the mtDNA Lineage Markers

Those samples that had amplified successfully were then subjected to each of five restriction enzyme digests—DdeI (13394)/AluI(13397), HaeIII(663), HincII(13259) and AluI (5176)—acknowledged to be characteristic of extant Asian and Asian-derived populations (Ward, et al., 1991; Stone and Stoneking, 1993; Wrischnik, et al., 1987; Merriwether, et al., 1996). The presence of the 9 base-pair deletion, due to its prevalent association with Asian populations, has been referred to as the "Asian Tag" (Shields, et al., 1993) and it used by researchers to trace migrations of Asian and Asian-derived populations (Shields, et al., 1993). The diagnostic ability of this length mutation has, however, come under question following the discovery of the "Asian Tag" in several individuals near Glasgow, Scotland (Thomas, et al., 1998). Thomas et al.'s (1998) findings suggest this length mutation had arisen at least twice within the history of human-mitochondrion association (Li, 1997). Alternatively, the mutation could be quite ancient and, outside Asian populations, have become quiet rare. Watkins, et al.'s (1999) finding of the deletion among individuals in southern India supports the presence of such relic mtDNA lineages (1999). Inasmuch as the restriction site fragment pattern by which a mtDNA lineage is characterized is transmitted exclusively by the females of that lineage, should a lineage stop producing females, that lineage, and the restriction site fragments with which it is associated, sill also cease. Therefore, it must not be ruled out that many such lineages may have existed but have not been recognized for lack of diagnostic markers.

These preliminary findings suggest the presence of such lineages. Analyses of ancient DNA from dental specimen #665 provides a case in point. Although mitochondria from this specimen have consistently cleaved when exposed to restriction enzymes HaeIII(663) and HincII(13259) (suggestive of Lineage A1), because the restriction sites for dDeI(10394)/AluI(10397) are also present, this individual might be better placed in Lineage D1, members of which do not possess the restriction enzyme site for HaeIII(663).

It cannot be overstated that the mtDNA haplotype markers elucidated by Merriwether et al., (1996) are representative of extant Asian and Asian-derived populations; as such, the may not characterize those now extinct. These findings, support previous mtDNA investigations of Anyang skeletal remains from which some of the teeth used in this study were derived (Graver, 1999). Before attempting to assign a specific lineage to remains, it will be essential to ascertain as much information as possible, not only from biomolecules or through morphological assessments, but through corroboration of other anthropological subdisciplines (e.g. archaeology, ethohistory, and linguistics).

Conclusion

The Reverse-Root-Canal protocol introduced in this paper provides a means by which fragile ancient biomolecules can be extracted from dental remains in a non-destructive manner. Furthermore, these data suggest the superiority of this protocol to that of traditionally practiced destructive methods. The enhanced presence of informative residues results from the acquisition of aDNA from dentin afforded maximum protection from exogenous contaminants in the canals and beneath the enameled crown (Zierdt, Hummel, Herrman, 1996). Therefore, because less organic material is required for DNA assays (DeGusta, Cook and Sensabaugh, 1994), this protocol will be invaluable in cases where remains are sparse or severely degraded (Evison, Smillie, Chamberlain, 1997). Collagen-derived dentin, acquired through non-destructive Reverse-Root-Canal, can also provide a means by which informative dental remains and associated archaeological sites can be radiometrically dated.

Finally it is hoped that museum curators and archaeologists, in light of the protocol described herein, will be less reluctant to part with dental specimens, their intact return assured. In so doing the chasm that has separated molecular from morphological research since the former's inception may be bridged, and bioarchaeology will be able to proceed aided by the additional perspective afforded by molecular assays.

Literature Cited

Alexandersen V and O Carlson (1998) Supernumerary Roots of Mandibular Molar Teeth. In Lukacs JE (ed): *Human Dental Development, Morphology and Pathology*. University of Oregon Anthropological Papers 54, pp. 201–214

Ariyaratnam MT, Wilson MA, Mackie, IC and AS Blinkhorn (1997) A comparison of surface roughness and composite/ enamel bond strength of human enamel following the application of the Nd:YAG laser and etching with phosphoric acid. Dent Mater. 13(1):51–55

Behrensmeyer AK (1975) Taphonomy and Paleoecology in the Hominid Fossil Record. Yrbk Phys Anthropol 19:36–50

Blakely RL and L Beck (1984) Tooth-Tool Use Versus Dental Mutilation: A Case Study From the Prehistoric Southeast. Midcontinental Journal of Archaeology 9:268–284

Brace CL (1975) Comment on "Did La Ferrassie I Use His Teeth as tools? Curr. Anthropology 16:396–397

Bullington J (1991) Dental microwear of prehistoric juveniles from the lower Illinois River Valley. Am. J. Phys. Anthropol. 84:59–74

Cavalli-Sforza LL and AWF Edwards (1967) Phyogenetic Analysis Models and Estimation Procedures. Am. J. Hum. Genet. 19(3):233–257

Cavalli-Sforza LL, Piazza A, Menozzi P, and J Mountain (1988) Reconstruction of human evolution: Bringing together genetic, archaeological and linguistic data. Proc. Natl. Acad. Sci. U.S.A. 85:6002–6006

Cavalli-Sforza LL, Menozzi P and J Mountain (1993) Demic Expansions and Human Evolution. Science 59:639–646

Cavalli-Sforza LL, Menozzi P and A Piazza (1994) *The History and Geography of Human Genes*. Princeton University Press Cavalli-Sforza LL (1998) The Chinese Human Genomic Diversity Project. Proc. Natl. Acad. Sci. U.S.A. 98(11501–11503

Chang KC (1976) *Early Chinese Civilization: Anthropological Perspectives*. Harvard University Press: Cambridge Colson IB, Bailey JF, Vercauteren M, Sykes BC and REM Hedges (1997) The Preservation of Ancient DNA and Bone Diagenesis. Ancient Biomolecules 1(2):109–117

DeGusta D, Cook C and G Sensabaugh (1994) Dentin as a source of ancient DNA. Ancient DNA Newsletter 2(1):13

Evison MP, Smillie DM, Chamberlain AT (1997) Extraction of Single-Copy Nuclear DNA from Forensic Specimens with a Variety of Postmortem Histories. J. Forensic Sci. 42(6):1032–1038

Francalacci P (1998) DNA Analysis on Ancient Desiccated Corpses from Xinjiang (China): Further Results. In Mair V (ed): *The Bronze Age and Early Iron Age Peoples of Eastern Central Asia*. Philadelphia, University of Pennsylvania Press, pp. 537–547

Ginter C, Issel-Tarver L, and MC King (1992) Identifying individuals by sequencing mitochondrial DNA from teeth. Nat. Genet. 2:135–138

Graver AM (1999) Ancient DNA: A Biomolecular Investigation of Human Remains From the Shang Dynasty Heiheru Site at Anyang, China (unpublished Master's thesis)

Grine FE and RE Kay (1988) Early hominid diets from quantitative image anlaysis of dental microwear. Nature 333:765–768

Hagelberg E and JB Clegg (1991) Isolation and characterization of DNA from archaeological bone. Proc. R. Soc. Lond. Biol. 244:45–52

Hagelberg E (1994) Dried Samples: Hard Tissues Mitochondrial DNA from Ancient Bones. In Hummel S and B Herrmann (eds): *Ancient DNA*. New York, Springer-Verlag, pp. 195–204

Hagelberg E, Kayser M, Nagy M, Roaer L, Zimdahl H, KrawczakM, Lio and W Schiefenhovel (1999) Molecular genetic evidence for the settlement of the Pacific: analysis of mitochondrial DNA Y chromosome and HLA markers. Phil. Trans. R. Soc. Lond. B 354:141–152

Handt O, Krings M, WardRH and S Paabo (1996) The Retrieval of Ancient Human DNA Sequences. Americna Journal of Human Genetics 59:368–376

Hillson S (1996) *Dental Anthropology*. Cambridge, Cambridge University Press

Hoss M and S Paabo (1993) Silica base method of DNA extraction from ancient bone. Nucleic Acids Res. 21:3913–3914

Irish JD (1998) Ancestral dental traits in recent Sub-Saharan Africans and the origins of modern humans. J. Hum. Evol. 34:81–98

Jacobi KP, Collins Cook D, Corruccini RS and JS Handler (1992) Congenital syphilis in the past: slaves at Newton Plantation, Barbados, West Indies. Am. J. Hum. Genet. 32:396413

Jeffreys AJ, Allen MJ, Hagelberg E and A Sonnberg (1992) Identification of the Skeletal Remains of Josef Mengele by DNA Analysis. Forensic Scient International 56:65–76

Katzenberg MA, Saunders SR and WR Fitzgerald (1993) Age Differences in Stable Carbon and Nitrogen Ratios in Population of Prehistoric Maize Horticulturists. Am. J. Phys. Anthropol. 90:267–281

Langsjoen O (1998) Diseases of the dentition. In Aufderheide A C and C Rodriguez-Martin (eds): *The Cambridge Encyclopedia of Paleopathology*, Cambridge, Cambridge University Press, pp. 393–412

Lassen C, Hummel S and B Herrmann (1994) Comparison of DNA extraction and amplification from ancient bone and mummified soft tissue. Int. J. Legal Med. 107:152–155

Li WH (1997) Chapter 13: Genome Organization and Evolution in *Molecular Evolution* Sinauer Associates, Inc., Sunderland Merridether D A, Hall W W, Vahlne A and R E Ferrell (1996) mtDNA Variation Indicates Mongolia May Have Been the Source for the Founding Population for the New World. Am. J. Hum. Gen. 59:204–212

Molto, J E (1999) Laboratory Techniques (in press)

Owsley DW and DT Bellande (1982) Culturally Induced Dental Alterations in a Historic Cherokee Skeletal Sample. Journal of Cherokee Studies 7:82–84

Paabo S (1990) Amplifying ancient DNA. In Innis M A, Gelfand D H, Sninski J J, and T J White (ed): *PCR Protocols: A Guide to Methods and Applications.* San Diego, Academic, pp. 159–166

Poinar H N, Hoss H, Bada L L and S Paabo (1996) Amino Acid Racemization and the Preservation of Ancient DNA. Science 272:864–866

Rollo F and L Marota (1999) How microbial ancient DNA, found in association with human remains, can be interpreted. Phil. Trans. R. Soc. Lond. B. 954:111–119

Schwartz T R, Schvartz E A, Miezerski L, McNally, and L L Kobilinsky (1991) Characterization of Deoxyribonucleic Acid (DNA) Obtained from Teeth Subjected to Various Environmental Conditions. J. Forensic Sci. 36(4) :979–990

Scott G R and C G Turner II (1997) *The Anthropology of Modern Human Teeth.* Cambridge, Cambridge University Press Shields G F, Schmiechen, A M, Frazier, B L, Redd, A, Volevoda, M I, Redd, J K, and R H Ward (1993) mtDNA sequences suggest a recent evolutionary divergence for Beringian and northern North American populations. Am. J. Hum. Genet. 53:549–562

Shields G F, Hecker K, Voevoda M I and J K Reed (1992) Absence of the Asian-specific Region V Mitochondrial Marker in Native Beringians. Am. J. Hum. Genet. 50:758–765

Smith B C, Fisher D L, Weedn V W, Warnock G R, and M Holland (1993) A Systematic Approach to the Sampling of Dental DNA. J. Forensic Sci. 38(5):1194–1209

Stone A C, and M Stoneking (1993) Ancient DNA from a Pre-Columbian Amerindian Population. Am. J. Phys. Anthropol. 92:463–471

Sutcliffe J G (1978) Complete Nucleotide Sequence of the *Escherhia coli* plasmid. *Cold Spring Harbor Symposium Quantitative Biology* 43:77–90

Szathmary E J E (1984) Peopling of North America: clues form genetic studies. Out of Asia: peopling the Americas and the Pacific in Journal of Pacific History 19, Kirk R and EJE Szathmary (eds.) pp. 79–104

Thomas M G, Cook C E, Miller K W, Waring M J and E Hagelberg (1998) Molecular Instability in the CO II-tRNA (Lys) intergenic region of the human mitochondrial genome: multiple origins of the 9-bp deletion and heteroplasmy for expanded repeats. Phil. Trans. R. Soc. Lond. B. 1998 353(1371):955–965

Tylka D F and G P Stewart (1994) Comparison of acidulated phosphate fluoride gel and hydrofluoric acid etchants for porcelain-composite repair. J. Prosthet. Dent. 72:121–127

Ungar P S and M A Spencer (1999) Incisor Microwear, Diet and Tooth Use in Three Amerindian Populations. Am. J. Phys. Anthropol. 109:387–396

Walker P L (1976) Wear striation on the incisors of ceropithecoid monkeys as an index of diet and habitat preference. Am. J. Phys. Anthropol. 45:299–308

Ward R H, Frazier B L, Dew-Jager K, S Paabo (1991) Extensive mitochondrial diversity within a single Amerindian tribe. Proc. Natl. Acad. Sci. U.S.A. 88:8720–8724

Watkins WS, Bamshad M, Dixon M E, Bhaskara B, Rao J M, Naidu P G, Reddy B V R, Prasad P K, Das P C, Reddy P B, Gai A, Bhanu Y S, Kusuma J K, Lum P, Fischer, and L B Jorde (1999) Multiple Origins of the mtDNA 9-bp Deletion in Populations of South India. Am. J. Phys. Anthropol. 109:147–158

Wrischnik L A, Higuchi R G, Stoneking M, Erlich H A, Arnheim N, and A C Wilson (1987) Length mutations in human mitochondrial DNA: Direct sequencing of enzymatically amplified DNA. Nucleic Acids Res. 15:529–542

Yang D Y, Eng B, Waye J S, Dudar J C and S R Saunders (1998) Technical Note: Improved DNA Extraction From Ancient Bones Using Silica-Based Spin Columns. Am. J. Phys. Anthropol. 105:539–543

Zhao T (1998) The Uyghurs, a Mongoloid-Caucasoid Mixed Population: Genetic Evidence and Estimates of Caucasian Admixture in the Peoples Living in Northwest China. *The Bronze Age and Early Iron Age Peoples of Eastern Central Asia,* Mair V (ed) Institute for the Study of Man, Inc. and University of Pennsylvania Museum Publications Zierdt, H., Hummel, S., and B. Herrmann (1996) Amplification of Human Short Tandem Repeats from Medieval Teeth and Bone Samples, Hum. Biol. 68(2):185–199

What is claimed is:

1. A nondestructive method for extracting nucleic acid-rich dentin from teeth comprising a) obtaining teeth to be studied b) generating a canal beginning at the apex, wherein the canal is generated with endodontic files beginning with a small endodontic file followed by larger endodontic files until a canal is generated directly beneath the enameled crown of the tooth c) collecting dentin from the canal d) extracting nucleic acid from the dentin.

* * * * *